US012618039B2

(12) United States Patent
Abe et al.

(10) Patent No.: US 12,618,039 B2
(45) Date of Patent: May 5, 2026

(54) INCUBATOR

(71) Applicant: ESPEC CORP., Osaka (JP)

(72) Inventors: Koichi Abe, Osaka (JP); Hiroshi Yata, Osaka (JP); Kenji Ashida, Osaka (JP); Yusuke Ueda, Osaka (JP)

(73) Assignee: ESPEC CORP., Osaka (JP)

( * ) Notice: Subject to any disclaimer, the term of this patent is extended or adjusted under 35 U.S.C. 154(b) by 917 days.

(21) Appl. No.: 17/660,764

(22) Filed: Apr. 26, 2022

(65) Prior Publication Data

US 2022/0340858 A1 Oct. 27, 2022

(30) Foreign Application Priority Data

Apr. 27, 2021 (JP) ................................. 2021-074677

(51) Int. Cl.
*C12M 1/00* (2006.01)
*C12M 1/34* (2006.01)
(52) U.S. Cl.
CPC .................................... *C12M 41/14* (2013.01)
(58) Field of Classification Search
CPC ............................... C12M 41/14; C12M 41/12
See application file for complete search history.

(56) References Cited

FOREIGN PATENT DOCUMENTS

| | | |
|---|---|---|
| JP | 2001-190268 A | 7/2001 |
| JP | 2006-275326 A | 10/2006 |
| JP | 2011-110033 A | 6/2011 |
| JP | 2016-109682 A | 6/2016 |

*Primary Examiner* — Lydia Edwards
(74) *Attorney, Agent, or Firm* — Studebaker Brackett PLLC

(57) ABSTRACT

An incubator includes: a housing which is divided into a thermostatic chamber and an air-conditioning chamber and allows first air to circulate between the thermostatic chamber and the air-conditioning chamber; and an air conditioner that regulates a temperature of the first air in the air-conditioning chamber. A channel through which the first air flows is formed in the air-conditioning chamber. The air conditioner includes: a supply unit having a supply port for supplying second air colder than the first air to the channel; an upstream fan which is arranged upstream of the supply port and allows the first air in the thermostatic chamber to flow into the channel; and a downstream fan which is arranged downstream of the supply port, mixes the second air with the first air, and allows the first air mixed with the second air to flow from the channel into the thermostatic chamber.

10 Claims, 4 Drawing Sheets

LEFT ⟷ RIGHT

RIGHT ⟷ LEFT

INCUBATOR

CROSS-REFERENCE TO RELATED APPLICATION

This application claims priority to Japanese Patent Application 2021-074677 filed on Apr. 27, 2021. The disclosures of the application including the specifications, the drawings, and the claims are hereby incorporated by reference in their entirety.

FIELD

The present disclosure relates to an incubator.

BACKGROUND

An incubator used for cell culture and other processes has been known. For example, Japanese Unexamined Patent Publication No. 2011-110033 discloses an incubator including a thermostatic chamber (cultivation chamber) and an air-conditioning chamber. The incubator circulates air cooled or heated in the air-conditioning chamber between the thermostatic chamber and the air-conditioning chamber to control the temperature of the thermostatic chamber to a set temperature.

SUMMARY

Uniform temperature distribution is one of important factors for the thermostatic chamber of the incubator. The incubator of Japanese Unexamined Patent Publication No. 2011-110033 still has room for improvement in the uniform temperature distribution.

In view of the foregoing background, the present disclosure has been achieved to make the temperature distribution in the thermostatic chamber uniform.

The present disclosure is directed to an incubator including: a housing which is divided into a thermostatic chamber and an air-conditioning chamber and allows first air to circulate between the thermostatic chamber and the air-conditioning chamber; and an air conditioner that regulates a temperature of the first air in the air-conditioning chamber. A channel through which the first air flows is formed in the air-conditioning chamber. The air conditioner includes: a supply unit having a supply port for supplying second air colder than the first air to the channel; an upstream fan which is arranged upstream of the supply port and allows the first air in the thermostatic chamber to flow into the channel; and a downstream fan which is arranged downstream of the supply port, mixes the second air with the first air, and allows the first air mixed with the second air to flow from the channel into the thermostatic chamber.

In this configuration, the second air is supplied by the supply unit to the channel of the air-conditioning chamber, and the first air flowing through the channel is cooled to a desired temperature when mixed with the second air. The downstream fan allows the first air regulated to the desired temperature to flow from the air-conditioning chamber into the thermostatic chamber, and the upstream fan allows the first air in the thermostatic chamber to flow into the channel of the air-conditioning chamber. Thus, the thermostatic chamber is controlled to the desired temperature.

The supply port is arranged between the upstream fan and the downstream fan. Thus, the upstream fan forces the first air into the second air supplied from the supply port. This accelerates the mixing of the first air and the second air.

Further, the downstream fan sucks the first air mixed with the second air. The suction by the downstream fan agitates the first air to further accelerates the mixing of the first air and the second air. This makes the temperature of the first air uniform. Supply of the first air with the uniform temperature to the thermostatic chamber can make the temperature distribution in the thermostatic chamber uniform.

A width direction of the channel may be orthogonal to a flow direction in the channel. The supply unit may include a plurality of ducts each allowing the second air to flow through and having the supply port. The supply ports of the plurality of ducts may be arranged at different positions in the width direction in the channel.

For example, if the second air is supplied through a single duct having a supply port, the flow rate of the second air supplied through the supply port may vary. This makes it difficult to supply the second air evenly in the width direction of the channel, resulting in uneven mixing ratio between the first air and the second air.

In the above-described configuration, in contrast, the supply unit includes the plurality of ducts each allowing the second air to flow through and having the supply port. The supply ports of the plurality of ducts are arranged at different positions in the width direction in the channel Thus, the second air can be supplied at a suitable flow rate to the supply ports through the ducts. The supply ports arranged side by side in the width direction can supply the second air evenly in the width direction of the channel. This makes the mixing ratio between the first air and the second air uniform in the width direction, and thus, makes the temperature distribution of the first air mixed with the second air uniform in the width direction.

The upstream fan may include a plurality of upstream fans arranged at different positions in the width direction in the channel.

In this configuration, the plurality of upstream fans are arranged, increasing the flow rate of the first air forced into the channel from the thermostatic chamber. This accelerates the mixing of the first air and the second air. Moreover, the plurality of upstream fans are arranged at different positions in the width direction of the channel, making the flow rate of the first air sucked into the channel from the thermostatic chamber uniform in the width direction of the channel. The first air is forced into the second air evenly in the width direction of the channel. This makes the mixing ratio between the first air and the second air uniform in the width direction.

The downstream fan may include a plurality of downstream fans arranged at different positions in the width direction in the channel.

In this configuration, the plurality of downstream fans are arranged, increasing the flow rate of the first air mixed with the second air and sucked into the downstream fans. This accelerates the mixing of the first air and the second air. Moreover, the plurality of downstream fans are arranged at different positions in the width direction in the channel, making a degree of mixing of the first air and the second air uniform in the width direction.

The incubator of the present disclosure may further include an exhaust fan that discharges the first air out of the housing.

In this configuration, for example, the exhaust fan discharges the first air out of the housing in an amount equal to the amount of the second air supplied through the supply port. This keeps the pressure in the thermostatic chamber from increasing, i.e., keeps the pressure in the thermostatic chamber constant.

The air conditioner may further include a heater which is arranged downstream of the supply port in the channel and heats the first air.

In this configuration, the first air is once cooled to a temperature below a desired temperature when the second air colder than the first air is supplied from the supply port to the channel. Thereafter, the first air is reheated by the heater to the desired temperature. This allows regulation of the temperature of the first air in a wider range.

The heater may be arranged downstream of the downstream fan in the channel.

In this configuration, the downstream fan is arranged upstream of the heater. This keeps the first air heated by the heater from passing through the downstream fan, and keeps the temperature of the downstream fan from increasing.

The housing may be placed and used in a room in which a temperature of air is regulated, and the supply unit may supply the air in the room as the second air to the channel.

In this configuration, the second air supplied to the channel by the supply unit is the temperature-regulated air in the room where the housing is placed. Specifically, the supply unit just supplies the second air without regulating the temperature of the second air. Even in such a case, the supply unit can supply the second air with a stable temperature. Further, the supply unit requires no refrigerator or any other devices, i.e., has no compressor which is a vibrating body included in the refrigerator. This can reduce the vibration of the incubator.

The supply unit may further include an intake fan that supplies the air in the room to the channel.

In this configuration, the air in the room is forced to enter the channel when the intake fan is operated. This can easily maintain the flow rate of the second air supplied as a source for cooling the first air.

The room may be a clean room.

In this configuration, the air with a high cleanliness level is supplied to the channel because the second air is the air in the clean room. Thus, a filter or any other devices for cleaning the second air is no longer necessary. This is particularly effective for the incubator that often requires the thermostatic chamber to keep a certain cleanliness level.

The incubator of the present disclosure can make the temperature distribution in the thermostatic chamber uniform.

DESCRIPTION OF EMBODIMENTS

Figure 1:
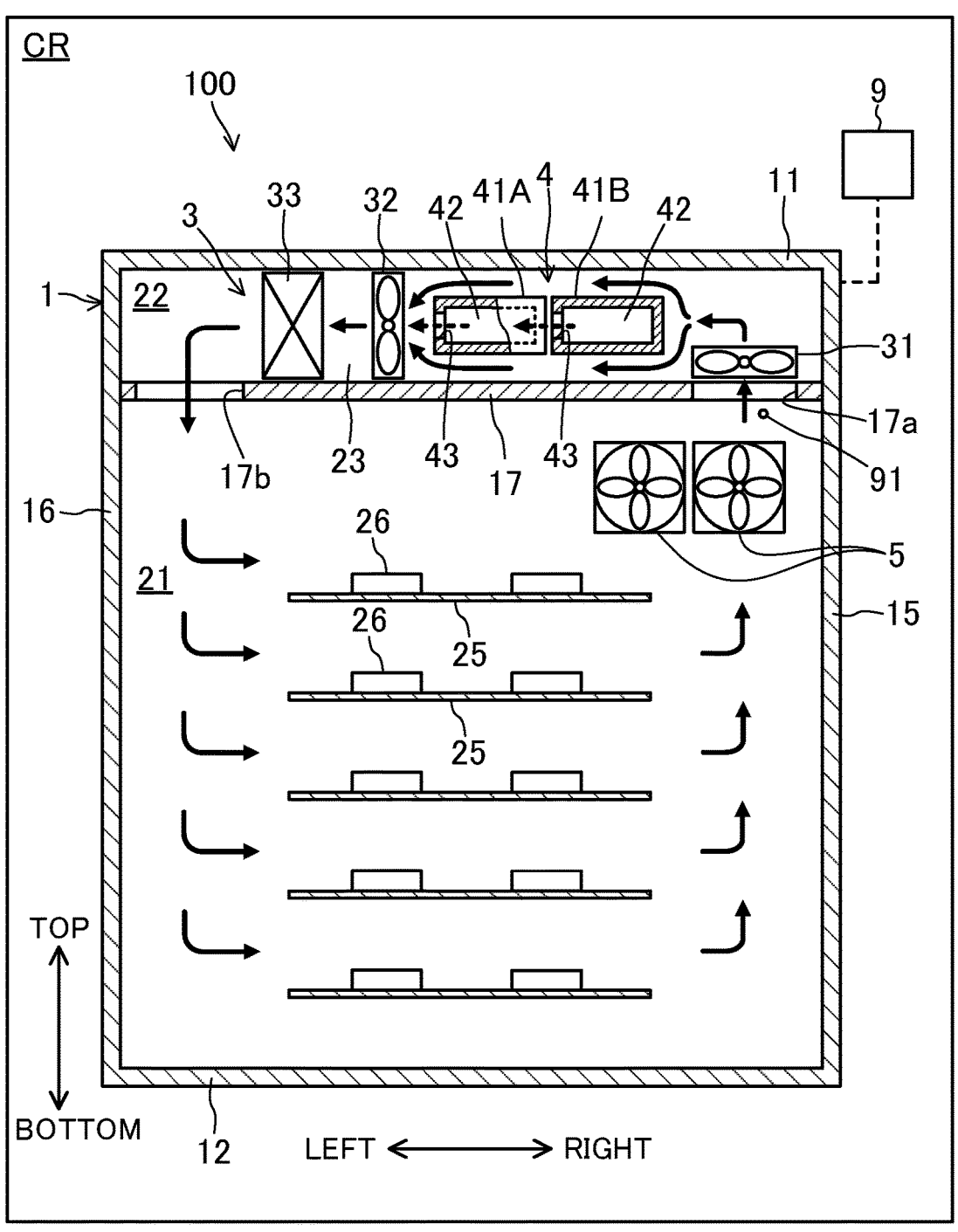
FIG. 1 is a cross section illustrating the inside of an incubator as viewed from the front.

Exemplary embodiments will be described in detail below with reference to the drawings. FIG. 1 is a cross section illustrating the inside of an incubator 100 as viewed from the front.

The incubator 100 includes a housing 1 and an air conditioner 3. The incubator 100 is used for, for example, a cell culture process and a shaking apparatus, and provides an ambient environment required for the process and the apparatus.

The housing 1 is divided into a thermostatic chamber 21 and an air-conditioning chamber 22. The housing 1 allows first air (see solid arrows in FIGS. 1 to 3) to circulate between the thermostatic chamber 21 and the air-conditioning chamber 22. The air conditioner 3 regulates the temperature of the first air in the air-conditioning chamber 22. The first air circulates between the thermostatic chamber 21 and the air-conditioning chamber 22 in the housing 1, and has its temperature controlled in the air-conditioning chamber 22. Thus, the first air having a desired temperature is supplied to the thermostatic chamber 21.

The housing 1 is placed in a clean room CR. The clean room CR is an example of a room in which the temperature of the air is regulated.

Specifically, the housing 1 is formed in a substantially rectangular parallelepiped box shape. The housing 1 has a ceiling wall 11, a bottom wall 12, a front wall 13, a rear wall 14, a right wall 15, and a left wall 16. The housing 1 further includes a divider wall 17 that divides an inside space into an upper space and a lower space. The lower space in the housing 1 below the divider wall 17 is the thermostatic chamber 21, and the upper space in the housing 1 above the divider wall 17 is the air-conditioning chamber 22. The divider wall 17 is provided with inlets 17a and an outlet 17b that allow the thermostatic chamber 21 and the air-conditioning chamber 22 to communicate with each other. The inlets 17a are formed in a right end portion of the divider wall 17, and the outlet 17b is formed in a left end portion of the divider wall 17.

The thermostatic chamber 21 is a space kept at a desired temperature, and is used as, for example, a cultivation chamber for culturing cells. The thermostatic chamber 21 has a plurality of shelf boards 25 extending in a horizontal direction. The shelf boards 25 are arranged at intervals in a vertical direction. For example, petri dishes 26 each containing a medium for culturing the cells are placed on the shelf boards 25.

A channel 23 through which the first air flows is formed in the air-conditioning chamber 22. The channel 23 extends from the inlets 17a to the outlet 17b. In this example, a fluid flows in the channel 23 substantially in the horizontal direction. More specifically, the fluid flows in the channel 23 from the right to the left in the horizontal direction.

Figure 2:
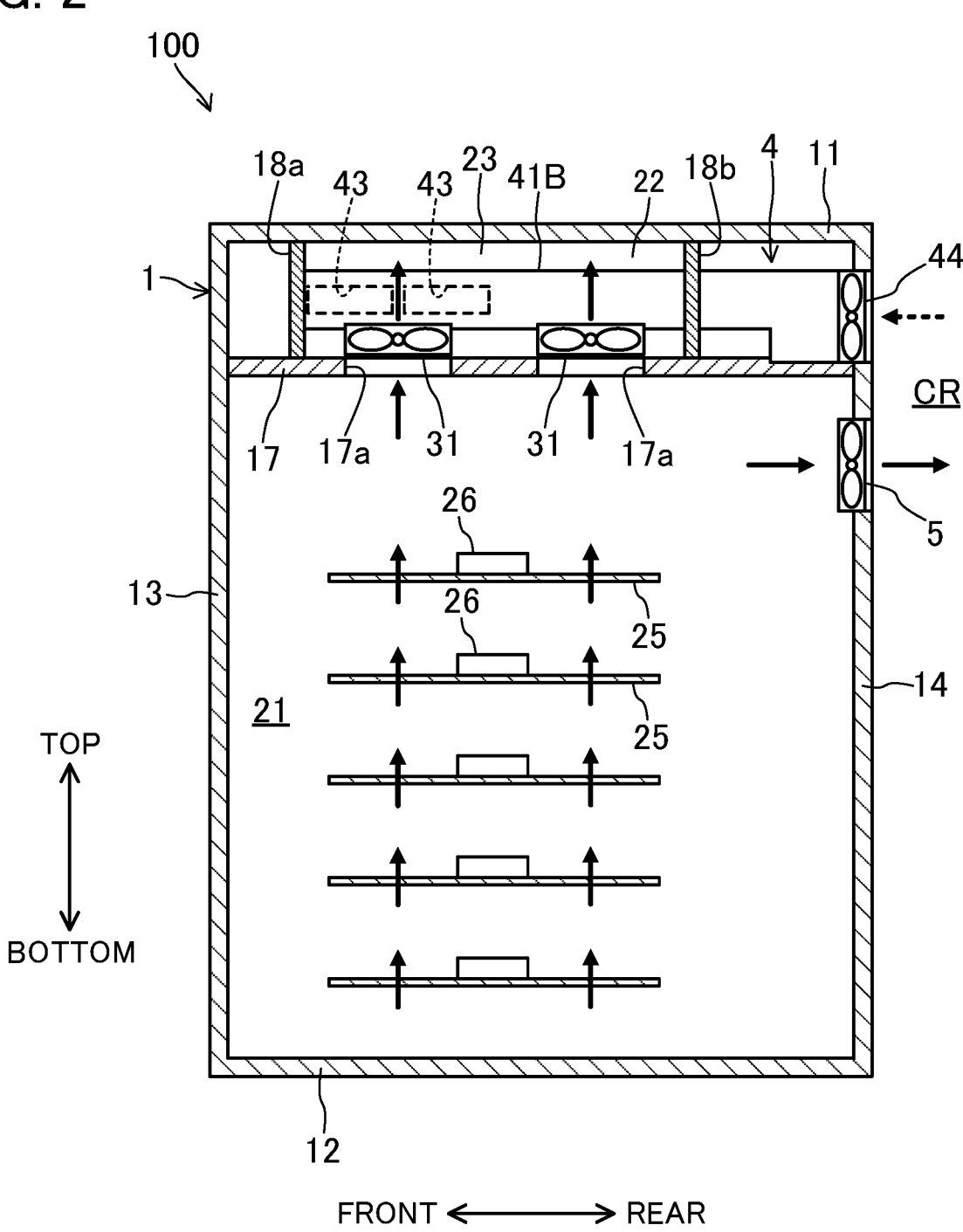
FIG. 2 is a cross section illustrating the inside of the incubator as viewed from the right.

The channel 23 spreads in a width direction orthogonal to the flow direction in the channel 23. Specifically, in the direction orthogonal to the flow direction, the channel 23 has a flat cross-sectional shape extending in a lengthwise direction and a widthwise direction orthogonal to each other as shown in FIG. 2. More specifically, the channel 23 is relatively long in the front-rear direction of the housing 1 and relatively short in the vertical direction of the housing 1, i.e., has a horizontally-oriented, substantially rectangular cross-sectional shape. In this example, the lengthwise direction of the cross-sectional shape of the channel 23, i.e., the front-rear direction of the housing 1, will be referred to as the width direction of the channel 23.

The housing 1 further includes two divider walls 18a and 18b that define the width of the channel 23. The two divider walls 18a and 18b are spaced from each other in the front-rear direction of the housing 1 (i.e., the width direction of the channel 23) in the air-conditioning chamber 22.

The air conditioner 3 includes a supply unit 4 that supplies second air (see dashed arrows in FIGS. 1 to 3) colder than the first air, an upstream fan 31, and a downstream fan 32. The air conditioner 3 further includes a heater 33.

The supply unit 4 supplies the air in the clean room CR as the second air to the channel 23. Specifically, the supply unit 4 includes a plurality of ducts, i.e., a first duct 41A and a second duct 41B. The inside of each of the first and second ducts 41A and 41B forms a supply path 42 through which the second air flows. The first and second ducts 41A and 41B have upstream ends opening in the rear wall 14. The housing 1 is placed in the clean room CR, and thus, the air in the clean room CR is present outside the rear wall 14. The supply paths 42 in the first and second ducts 41A and 41B communicate with the clean room CR through the openings in the rear wall 14.

Figure 3:
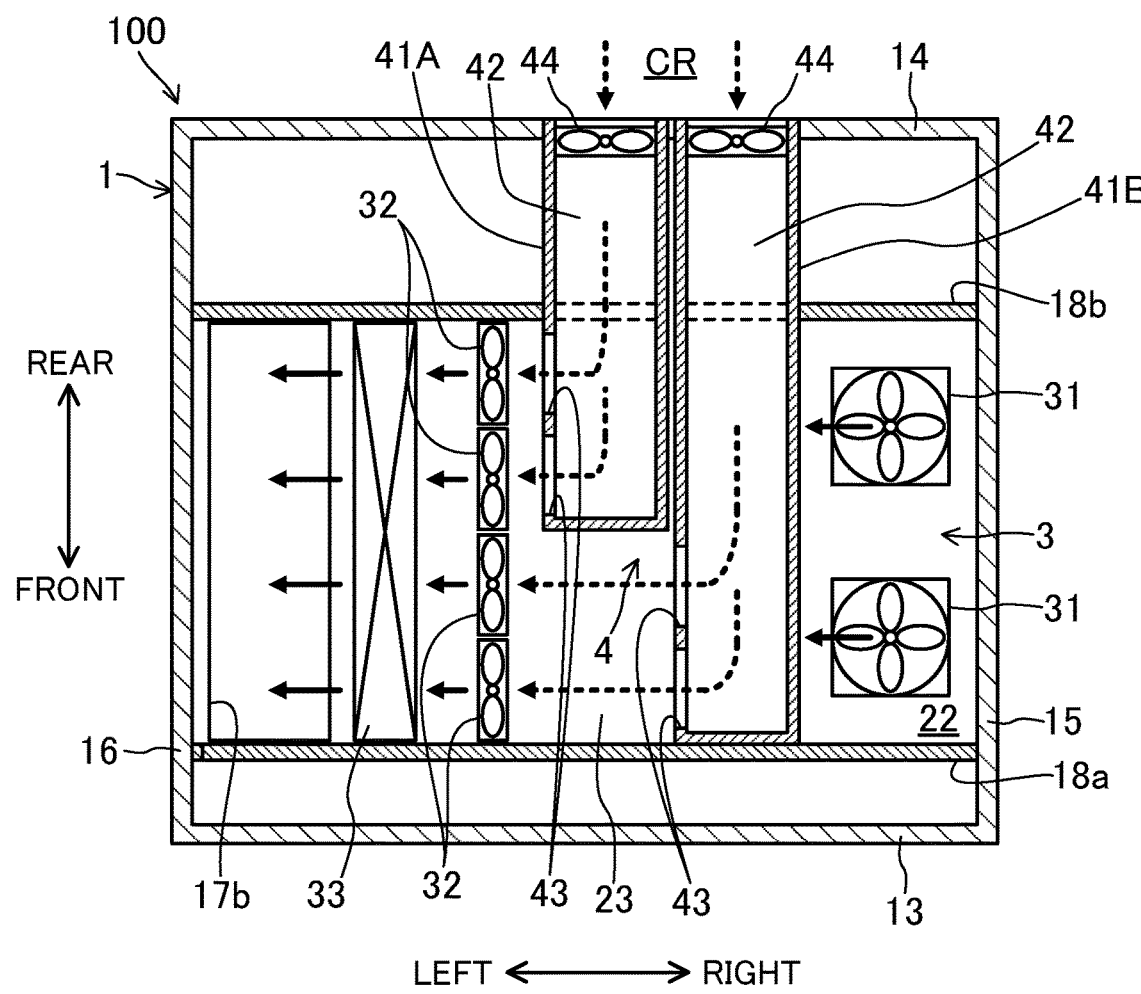
FIG. 3 is a cross section illustrating the inside of the incubator as viewed from above.
Figure 4:
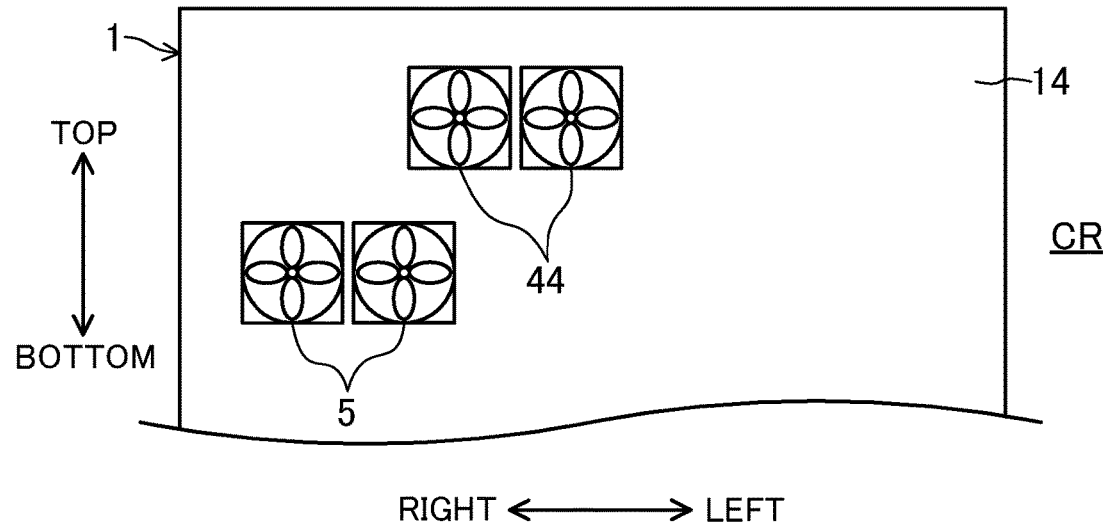
FIG. 4 is a rear view of the incubator, with some components omitted.

The supply unit 4 further includes an intake fan 44 that supplies the air in the clean room CR to the channel 23. Specifically, as shown in FIGS. 2 to 4, the intake fan 44 is arranged at each of the upstream ends of the first and second ducts 41A and 41B. The intake fans 44 are attached to the rear wall 14. The intake fans 44 allow the air in the clean room CR to flow into the supply paths 42.

The first and second ducts 41A and 41B penetrate the channel 23. The first and second ducts 41A and 41B extend in the channel 23 in the width direction of the channel 23 (i.e., the front-rear direction of the housing 1). The first and second ducts 41A and 41B have downstream ends forming supply ports 43 that supply the second air to the channel 23. The supply paths 42 in the first and second ducts 41A and 41B communicate with the channel 23 through the supply ports 43.

Each of the ducts has the supply ports 43 arranged at different positions in the width direction in the channel 23. Specifically, the second duct 41B is arranged upstream of the first duct 41A in the flow direction in the channel 23. The second duct 41B extends to be closer to the front side of the housing 1 than the first duct 41A in the channel 23. The downstream end of the first duct 41A is provided with two supply ports 43 arranged side by side in the width direction of the channel 23. Likewise, the downstream end of the second duct 41B is provided with two supply ports 43 arranged side by side in the width direction of the channel 23. The two supply ports 43 of the second duct 41B are positioned closer to the front side of the housing 1 than the two supply ports 43 of the first duct 41A. That is, the two supply ports 43 of the first duct 41A and the two supply ports 43 of the second duct 41B, four supply ports in total, are arranged at different positions in the width direction of the channel 23. The two supply ports 43 of the second duct 41B are shifted to the upstream side in the flow direction in the channel 23 from the two supply ports 43 of the first duct 41A.

The upstream fan 31 is arranged upstream of the supply ports 43 in the channel 23. The upstream fan 31 allows first air in the thermostatic chamber 21 to flow into the channel 23. The upstream fan 31 includes a plurality of upstream fans arranged at different positions in the width direction in the channel 23. Specifically, the air conditioner 3 includes two upstream fans 31 as shown in FIGS. 1 to 3. The two upstream fans 31 are arranged upstream of the first and second ducts 41A and 41B that penetrate the channel 23. Two inlets 17a arranged side by side in the width direction of the channel 23 are formed in the right end portion of the divider wall 17 as shown in FIG. 2. Each of the two upstream fans 31 is arranged near the two inlets 17a to face an associated one of the two inlets 17a. That is, the two upstream fans 31 are arranged side by side in the width direction of the channel 23.

The downstream fan 32 is arranged downstream of the supply ports 43 in the channel 23, mixes the second air with the first air, and allows the first air mixed with the second air to flow from the channel 23 into the thermostatic chamber 21. The downstream fan 32 includes a plurality of downstream fans arranged at different positions in the width direction in the channel 23. Specifically, the air conditioner 3 includes four downstream fans 32 as shown in FIG. 3. The four downstream fans 32 are arranged downstream of the first and second ducts 41A and 41B that penetrate the channel 23. The four downstream fans 32 are arranged side by side in the width direction of the channel 23. Two of the four downstream fans 32 face the two supply ports 43 of the first duct 41A in the flow direction in the channel 23, and the remaining two downstream fans 32 face the two supply ports 43 of the second duct 41B in the flow direction in the channel 23.

The heater 33 is arranged downstream of the supply ports 43 in the channel 23 and heats the first air. Specifically, the heater 33 is arranged downstream of the downstream fans 32 in the channel 23 as shown in FIGS. 1 and 3. The heater 33 extends over the width of the channel 23. The heater 33 is arranged to face the four downstream fans 32 in the flow direction in the channel 23. The heater 33 is, for example, a heat transfer heater.

The incubator 100 further includes exhaust fans 5 that discharge the first air out of the housing 1 as shown in FIGS. 1, 2, and 4. Specifically, the incubator 100 includes two exhaust fans 5. The two exhaust fans 5 are provided on the rear wall 14 in the thermostatic chamber 21. That is, the thermostatic chamber 21 communicates with the clean room CR through the exhaust fans 5. More specifically, the two exhaust fans 5 are arranged near the divider wall 17 in the thermostatic chamber 21. Thus, the two exhaust fans 5 discharge part of the first air that has passed through the thermostatic chamber 21 out of the housing 1 just before entering the air-conditioning chamber 22.

The incubator 100 further includes a temperature sensor 91 that detects the temperature of the first air in the housing 1, and a controller 9 that controls the temperature of the first air based on the detection result of the temperature sensor 91.

The temperature sensor 91 is arranged in the thermostatic chamber 21 as shown in FIG. 1. Specifically, the temperature sensor 91 is arranged near the inlets 17a in the thermostatic chamber 21.

The controller 9 includes a control unit such as a processor, a storage, and a memory. The controller 9 receives a detection signal from the temperature sensor 91. The controller 9 outputs a control signal to the heater 33 to control the capacity of the heater 33. Specifically, the controller 9 regulates the output of the heater 33 so that the temperature of the first air detected by the temperature sensor 91 reaches a desired temperature.

How the incubator 100 configured in this manner operates will be described below.

When the upstream fans 31 and the downstream fans 32 are operated, a flow of the first air circulating between the thermostatic chamber 21 and the air-conditioning chamber 22 is generated in the housing 1.

Specifically, the downstream fans 32 allow the first air in the air-conditioning chamber 22 to flow into the thermostatic chamber 21. The divider wall 17 that defines the top of the thermostatic chamber 21 has the outlet 17b formed in its left end portion. The first air in the air-conditioning chamber 22 flows into an upper left portion of the thermostatic chamber 21 through the outlet 17b. The downstream fans 32 produce a downward air current in a relatively left portion of the thermostatic chamber 21, i.e., on the left of the shelf boards 25 in the thermostatic chamber 21.

The first air flowing downward on the left of the shelf boards 25 in the thermostatic chamber 21 passes between the shelf boards 25 and moves to the right in the thermostatic chamber 21.

The inlets 17a are formed in the right end portion of the divider wall 17. The upstream fans 31 are arranged near the inlets 17a in the air-conditioning chamber 22. Thus, the suction by the upstream fans 31 produces an upstream air current on the right of the shelf boards 25 in the thermostatic chamber 21. The first air flows upward on the right of the shelf boards 25 in the thermostatic chamber 21, and enters the air-conditioning chamber 22 through the inlets 17a. At this time, the temperature sensor 91 detects the temperature of the first air entering the air-conditioning chamber 22.

In the air-conditioning chamber 22, the supply ports 43 of the first and second ducts 41A and 41B are positioned downstream of the inlets 17a in the channel 23. The intake fans 44 allow the air in the clean room CR to flow through the supply paths 42 in the first and second ducts 41A and 41B. The air in the clean room CR is supplied as the second air to the channel 23 from the supply ports 43.

The upstream fans 31 force the first air that has entered the channel 23 from the thermostatic chamber 21 through the inlets 17a to flow downstream in the channel 23. The first air flows around the first and second ducts 41A and 41B and passes near the supply ports 43. At this time, the second air is supplied to the first air through the supply ports 43. The second air, which is colder than the first air, lowers the temperature of the first air when mixed with the first air.

The first air mixed with the second air is forced by the upstream fans 31 and sucked by the downstream fans 32 to flow further downstream, and is sucked into the downstream fans 32. The downstream fans 32 evenly mix the second air with the first air, and blows out the first air mixed with the second air.

The first air blown out of the downstream fans 32 passes through the heater 33. The heater 33 heats the first air to raise the temperature of the first air. At this time, the controller 9 controls the output of the heater 33 based on the detection result of the temperature sensor 91. Thus, the temperature of the first air is regulated to a desired temperature.

The first air that has passed through the heater 33 and regulated to the desired temperature flows from the channel 23 into the thermostatic chamber 21 through the outlet 17b as described above.

In this manner, the first air circulates between the thermostatic chamber 21 and the air-conditioning chamber 22 in the housing 1. Thus, the temperature of the first air is regulated in the air-conditioning chamber 22 to the desired temperature.

For a constant pressure in the housing 1, the exhaust fans 5 discharge the first air out of the housing 1 in an amount corresponding to the amount of the second air supplied by the supply unit 4. Specifically, the exhaust fans 5 are provided near the divider wall 17 in the thermostatic chamber 21. Thus, part of the first air flowing upward on the right of the shelf boards 25 in the thermostatic chamber 21 is discharged to the clean room CR out of the housing 1 through the exhaust fans 5 without entering the air-conditioning chamber 22.

The incubator 100 configured as described above can make the temperature distribution in the housing 1 uniform.

Specifically, the supply ports 43 are arranged between the upstream fans 31 and the downstream fans 32 in the flow direction. That is, the fans (i.e., the upstream fans 31 and the downstream fans 32) are arranged on both the upstream and downstream sides of the supply ports 43 in the flow direction in the channel 23. The upstream fans 31 increase the flow rate of the first air supplied near the supply ports 43. This improves a degree of mixing of the first air and the second air near the supply ports 43. The "degree of mixing" is a degree indicating how evenly the first air and the second air are mixed. Further, the downstream fans 32, which are arranged downstream of the supply ports 43, suck the first air mixed with the second air near the supply ports 43. The suction by the downstream fans 32 agitates the first air and further improves the degree of mixing of the first air and the second air, making the temperature of the first air uniform. The first air having the uniform temperature supplied to the thermostatic chamber 21 makes the temperature distribution in the thermostatic chamber 21 uniform.

The supply unit 4 further includes the first and second ducts 41A and 41B, and the supply ports 43 of the first duct 41A and the supply ports 43 of the second duct 41B are arranged at different positions in the width direction in the channel 23. This allows the second air to be supplied from the supply ports 43 of the first and second ducts 41A and 41B to different positions in the width direction in the channel 23, reducing biased distribution of the second air in the width direction of the channel 23. Thus, the mixing ratio between the first air and the second air near the supply ports 43 is made uniform in the width direction.

The air conditioner 3 includes the plurality of upstream fans 31 arranged at different positions in the width direction in the channel 23. Provision of the plurality of upstream fans 31 increases the flow rate of the first air forced into the channel 23 from the thermostatic chamber 21. This improves the degree of mixing of the first air and the second air. Moreover, arranging the plurality of upstream fans 31 at different positions in the width direction makes the flow rate of the first air sucked from the thermostatic chamber 21 into the channel 23 uniform in the width direction of the channel 23. This makes the mixing ratio between the first air and the second air uniform in the width direction.

The air conditioner 3 includes the plurality downstream fans 32 arranged at different positions in the width direction in the channel 23. Provision of the plurality of downstream fans 32 increases the flow rates of the first air and the second air sucked into the channel 23 by the downstream fans 32 and accelerates the agitation of the first air and the second air. This improves the degree of mixing of the first air and the second air. Moreover, arranging the plurality of downstream fans 32 at the different positions in the width direction makes the mixing ratio between the first air and the second air uniform in the width direction.

The exhaust fans 5 are provided to discharge the first air out of the housing 1. This can keep the pressure in the thermostatic chamber 21 constant without increasing the pressure. Thus, the first air is easily supplied from the air-conditioning chamber 22 to the thermostatic chamber 21. In this example, in particular, the exhaust fans 5 provided in the thermostatic chamber 21 can directly discharge the first air in the thermostatic chamber 21 out of the housing 1. This can quickly keep the pressure in the thermostatic chamber 21 from increasing.

The heater 33 for heating the first air is provided downstream of the supply ports 43 in the channel 23. Thus, the first air that has flowed into the channel 23 is once cooled to a temperature below the desired temperature when mixed with the second air, and then reheated to the desired temperature by the heater 33. This method can regulate the temperature of the first air in a wider range, and allows the regulation of the temperature of the first air with high accuracy. The heater 33 is a heat transfer heater, and does not use a refrigerant circuit or any other devices. The heater 33 has no devices that cause vibration, such as a compressor. This can reduce the vibration generated by the incubator 100.

The heater 33, which is arranged downstream of the downstream fans 32, can keep the first air heated by the heater 33 from passing through the downstream fans 32. This can keep the temperature of the downstream fans 32 from increasing.

The housing 1 is placed in a room in which the temperature of the air is regulated, and the supply unit 4 supplies the air in the room as the second air into the channel 23. That is, the air in the room is supplied as a source for cooling the first air, requiring no refrigerator for cooling the first air. Thus, there is no compressor which is a vibrating body included in the refrigerator, and the vibration can be reduced. This is particularly effective for the incubator 100 used for, e.g., cell culture easily affected by the vibration.

The intake fans 44 are provided to supply the air in the room with the regulated temperature to the channel 23. When the intake fans 44 are operated, the flow rate of the second air supplied as the source for cooling the first air can be easily maintained.

The room with the regulated air temperature, which is the clean room CR, can supply the air with a high cleanliness level as the second air to the channel 23. Thus, a filter or any other devices for cleaning the second air is no longer necessary. This is particularly effective for the incubator 100 used for cell culture or any other processes because the thermostatic chamber 21 is required to keep a certain cleanliness level.

The incubator 100 achieves another object of reduced vibration of the incubator 100, in addition to the uniform temperature distribution in the thermostatic chamber 21. Specifically, the incubator 100 includes: the housing 1 divided into the thermostatic chamber 21 and the air-conditioning chamber 22 and allows the first air to circulate between the thermostatic chamber 21 and the air-conditioning chamber 22; and the air conditioner 3 that regulates the temperature of the first air in the air-conditioning chamber 22. The housing 1 is placed and used in the clean room CR (room) filled with the second air colder than the first air. The channel 23 through which the first air flows is formed in the air-conditioning chamber 22. The air conditioner 3 includes the supply unit 4 having the supply ports 43 for supplying the second air in the clean room CR to the channel 23, and the upstream fans 31 or the downstream fans 32 (fans) arranged in the channel 23 and allow the first air to circulate between the channel 23 and the thermostatic chamber 21. The air conditioner 3 mixes the second air with the first air and allows the first air mixed with the second air to flow from the channel 23 into the thermostatic chamber 21.

In this configuration, the first air circulates between the thermostatic chamber 21 and the air-conditioning chamber 22, and the supply unit 4 supplies the low-temperature second air to the first air in the air-conditioning chamber 22, thereby regulating the temperature of the first air. The supply unit 4 has no air conditioner such as a refrigerator. The supply unit 4 supplies the air in the clean room CR as the second air. The air in the clean room CR is regulated to be colder than the first air. That is, the supply unit 4 just supplies the second air without regulating the temperature of the second air. Even in such a case, the supply unit 4 can supply the second air at a stable temperature because the second air is the temperature-regulated air in the clean room CR. Further, the supply unit 4 having no refrigerator or any other devices reduces the vibration of the incubator 100. Specifically, the refrigerator may include devices that may cause vibration, such as a compressor. If such a device is placed on the housing 1 or on the floor where the housing 1 is placed, the vibration of the device may be transmitted to the housing 1, affecting the objects in the thermostatic chamber 21, such as the petri dishes 26. The supply unit 4 having no air conditioner such as the refrigerator can reduce the vibration transmitted to the housing 1.

Other Embodiments

Embodiments have just been described as examples of the technique disclosed in the present application. However, the present disclosure is not limited to those exemplary embodiments, but is also applicable to other embodiments which are altered or substituted, to which other features are added, or from which some features are omitted, as needed. Optionally, the components described in those embodiments may be combined to create a new embodiment. The components illustrated on the accompanying drawings and described in the detailed description include not only essential components that need to be used to overcome the problem, but also other unessential components that do not have to be used to overcome the problem. Therefore, such unessential components should not be taken for essential ones, simply because such unessential components are illustrated in the drawings or mentioned in the detailed description.

The thermostatic chamber 21 and the air-conditioning chamber 22 are arranged one above the other in the housing 1. However, the arrangement of these chambers is not limited to this example. For example, the thermostatic chamber 21 and the air-conditioning chamber 22 may be arranged side by side in the front-rear direction or the left-right direction. The air-conditioning chamber 22 may extend from the top to the side of the thermostatic chamber 21.

The numbers of the upstream fans 31, the downstream fans 32, the ducts, the supply ports 43, the intake fans 44, and the exhaust fans 5 are merely examples, and are not limited to those described above.

The intake fans 44 may be omitted. In this case, the supply ports 43 arranged in the channel 23 allow the air in the clean room CR to be sucked into the channel 23 through the ducts due to the ejector effect caused by the first air flowing through the channel 23.

For example, the upstream ends of the ducts may not extend from the rear wall 14. The ducts may extend from the ceiling wall 11. Alternatively, the supply unit 4 may have an opening formed in the wall forming the channel 23 and may have no ducts. For example, the supply unit 4 may have an opening formed in the ceiling wall 11 for communication between the outside of the housing 1 and the channel 23. When the second air flows through the supply paths 42 in the ducts in the width direction of the channel 23 as in the above example, the amount of the second air supplied from the supply ports 43 may vary in the width direction of the channel 23. On the other hand, when the ducts extend from the ceiling wall 11 or the opening is formed in the ceiling wall 11, the second air flows in the vertical direction of the housing 1, instead of the width direction of the channel 23.

Thus, the amount of the second air supplied from the supply ports 43 does not greatly vary in the width direction of the channel 23. For this reason, the supply ports 43 may be formed into a single opening extending in the width direction of the channel 23. In this case, the intake fan 44 can be arranged on the ceiling wall 11.

The exhaust fans 5 may be arranged in the air-conditioning chamber 22 instead of the thermostatic chamber 21.

The room where the housing 1 is placed is not limited to the clean room CR. The housing 1 can be placed in any room in which the temperature of the air is regulated.

The supply ports 43 are open in the channel 23 toward downstream fans 32 (i.e., toward the downstream side in the flow direction), but the opening direction of the supply ports is not limited to this example. The supply ports may open toward a direction orthogonal to the flow direction.

The width direction of the channel 23 is not limited to the front-rear direction of the housing 1. The width direction of the channel 23 may be any direction orthogonal to the flow direction in the channel 23. For example, when the channel 23 has a vertically-oriented cross-sectional shape which is longer in the vertical direction of the housing 1 than in the front-rear direction of the housing 1, the width direction of the channel 23 may be the vertical direction of the housing 1. In this case, the supply ports 43 of the first duct 41A and the supply ports 43 of the second duct 41B are arranged at different positions in the width direction in the channel 23, i.e., the vertical direction of the housing 1. The two upstream fans 31 can also be arranged in the channel 23 at different positions in the vertical direction of the housing 1. The plurality of downstream fans 32 can also be arranged at different positions in the channel 23 in the vertical direction of the housing 1.

If the first air can be cooled to the desired temperature when mixed with the second air, the heater 33 may be omitted.

Figure 5:
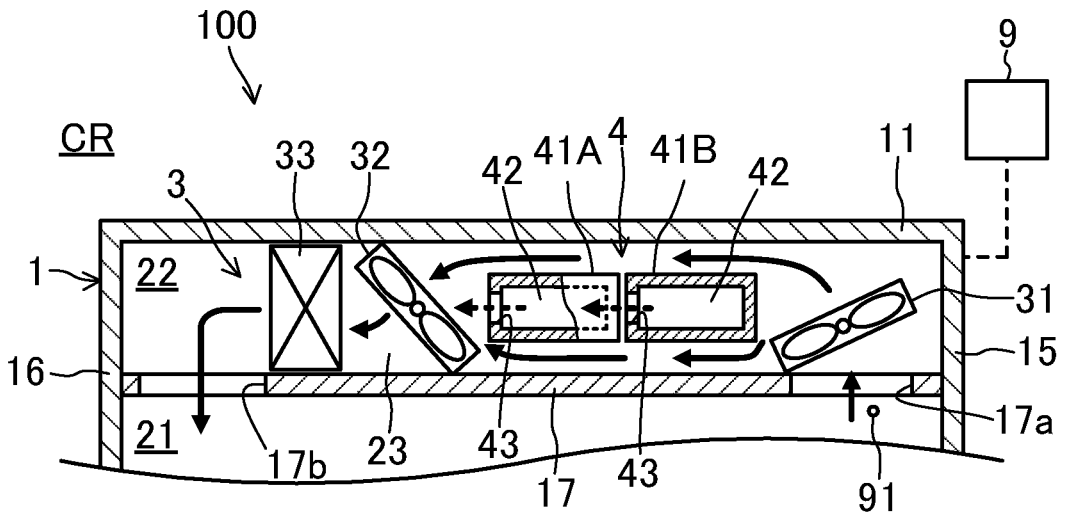
FIG. 5 is an enlarged cross section illustrating an air-conditioning chamber according to a first variation as viewed from the front.
Figure 6:
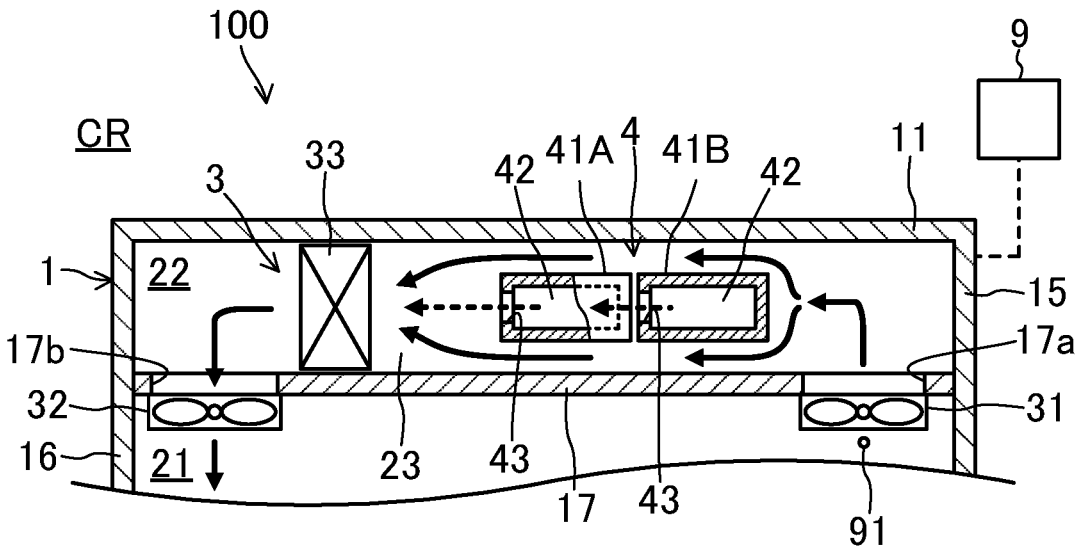
FIG. 6 is an enlarged cross section illustrating an air-conditioning chamber according to a second variation as viewed from the front.

The arrangement of the upstream fans 31 and the downstream fans 32 is not limited to the example described above. FIGS. 5 and 6 show variations of the arrangement of the upstream fans 31 and the downstream fans 32. FIG. 5 is an enlarged cross section illustrating an air-conditioning chamber 22 according to a first variation as viewed from the front. FIG. 6 is an enlarged cross section illustrating an air-conditioning chamber 22 of a second variation as viewed from the front.

For example, the upstream fans 31 may be tilted in the air-conditioning chamber 22 as shown in FIG. 5. The downstream fans 32 may be tilted in the air-conditioning chamber 22. Specifically, the upstream fans 31 are arranged near the inlets 17a in the air-conditioning chamber 22. An axis of rotation of each upstream fan 31 is tilted with respect to the vertical direction. The upstream fans 31 suck the first air in a direction obliquely upward to the left with respect to the inlets 17a. The downstream fans 32 are arranged near the outlet 17b in the air-conditioning chamber 22. An axis of rotation of each downstream fan 32 is tilted with respect to the vertical direction. The downstream fans 32 blow the air in a direction obliquely downward to the left with respect to the inlets 17a. In this configuration, relatively large upstream fans 31 or downstream fans 32 can be arranged even in a small air-conditioning chamber 22. Although the upstream fans 31 and the downstream fans 32 are both tilted in the example of FIG. 5, the fans are not limited to this example. At least one of the upstream fans 31 or the downstream fans 32 may be tilted.

Alternatively, the upstream fans 31 may be arranged on the divider wall 17 as shown in FIG. 6. The downstream fans 32 may also be arranged on the divider wall 17. The upstream fans 31 are in the thermostatic chamber 21 and attached to the divider wall 17 to cover the inlets 17a. Specifically, it is only required that the upstream fans 31 are arranged between the divider wall 17 and the supply ports 43 (including the case where the upstream fans 31 are attached to the divider wall 17). Thus, the upstream fans 31 allow the first air in the thermostatic chamber 21 to flow into the channel 23. The downstream fans 32 are in the thermostatic chamber 21 and attached to the divider wall 17 to cover the outlet 17b. Specifically, it is only required that the downstream fans 32 are arranged between the supply ports 43 and the divider wall 17 (including the case where the downstream fans 32 are attached to the divider wall 17). Thus, the downstream fans 32 allow the first air to flow from the channel 23 into the thermostatic chamber 21. The upstream fans 31 or the downstream fans 32 may be directly attached to the divider wall 17, or may be indirectly attached to the divider wall 17 with spacers or ducts interposed therebetween. Further, the heater 33 may be arranged upstream of the downstream fans 32 in the flow direction as shown in FIG. 6. In this case, the first air heated by the heater 33 is sucked into the downstream fans 32. This makes the temperature distribution of the first air heated by the heater 33 uniform. Although the upstream fans 31 and the downstream fans 32 are both arranged on the divider wall 17 in FIG. 6, the arrangement of the fans is not limited to this example. At least one of the upstream fans 31 or the downstream fans 32 may be arranged on the divider wall 17. At least one of the upstream fans 31 or the downstream fans 32 attached to the divider wall 17 may be tilted with respect to the divider wall 17.

What is claimed is:

1. An incubator, comprising:
   a housing which is divided into a thermostatic chamber and an air-conditioning chamber and allows first air to circulate between the thermostatic chamber and the air-conditioning chamber; and
   an air conditioner that regulates a temperature of the first air in the air-conditioning chamber, wherein
   a channel through which the first air flows is formed in the air-conditioning chamber,
   the air conditioner includes:
   a supply unit having a supply port for supplying second air colder than the first air to the channel;
   an upstream fan which is arranged upstream of the supply port in a flow direction in the channel and allows the first air in the thermostatic chamber to flow into the channel; and
   a downstream fan which is arranged downstream of the supply port in the flow direction, mixes the second air with the first air, and allows the first air mixed with the second air to flow from the channel into the thermostatic chamber,
   a width direction of the channel is orthogonal to the flow direction in the channel,
   the supply unit includes a plurality of ducts each extending in the channel in the width direction of the channel, allowing the second air to flow through and having the supply port, and
   the supply ports of the plurality of ducts are arranged at different positions in the width direction in the channel.

2. The incubator of claim 1, wherein
   the upstream fan includes a plurality of upstream fans arranged at different positions in the width direction in the channel.

3. The incubator of claim 1 or 2, wherein
the downstream fan includes a plurality of downstream fans arranged at different positions in the width direction in the channel.

4. The incubator of claim 1 or 2, further comprising:
an exhaust fan that discharges the first air out of the housing.

5. The incubator of claim 1 or 2, wherein
the housing is placed and used in a room in which a temperature of air is regulated, and
the supply unit supplies the air in the room as the second air to the channel.

6. The incubator of claim 5, wherein
the supply unit further includes an intake fan that supplies the air in the room to the channel.

7. The incubator of claim 5, wherein
the room is a clean room.

8. An incubator, comprising:
a housing which is divided into a thermostatic chamber and an air-conditioning chamber and allows first air to circulate between the thermostatic chamber and the air-conditioning chamber; and
an air conditioner that regulates a temperature of the first air in the air-conditioning chamber, wherein
the housing is placed and used in a room filled with second air colder than the first air, a channel through which the first air flows is formed in the air-conditioning chamber,
the air conditioner includes:
a supply unit having a supply port for supplying the second air in the room to the channel;
and a fan which is arranged in the channel and allows the first air to circulate between the channel and the thermostatic chamber,
the air conditioner mixes the second air with the first air and allows the first air mixed with the second air to flow from the channel into the thermostatic chamber,
a width direction of the channel is orthogonal to the flow direction in the channel,
the supply unit includes a plurality of ducts each extending in the channel in the width direction of the channel, allowing the second air to flow through and having the supply port, and
the supply ports of the plurality of ducts are arranged at different positions in the width direction in the channel.

9. The incubator of claim 1 or 2, wherein
the air conditioner further includes a heater which is arranged downstream of the supply port in the flow direction in the channel and heats the first air.

10. The incubator of claim 9, wherein
the heater is arranged downstream of the downstream fan in the flow direction in the channel.

* * * * *